United States Patent [19]

Lauterjung

[11] 4,376,439
[45] Mar. 15, 1983

[54] SUCTION BOTTLE FOR MEDICAL PURPOSES PARTICULARLY FOR THE CONNECTION OF DRAINAGE TUBES

[76] Inventor: Friedrich G. Lauterjung, Schallstr. 6, 5000 Cologne 41, Fed. Rep. of Germany

[21] Appl. No.: 137,154

[22] Filed: Apr. 4, 1980

[30] Foreign Application Priority Data

Apr. 28, 1979 [DE] Fed. Rep. of Germany ....... 2917332
Mar. 27, 1980 [DE] Fed. Rep. of Germany ....... 3011799

[51] Int. Cl.³ .............................................. A61M 1/00
[52] U.S. Cl. .................................. 128/276; 215/260; 128/760
[58] Field of Search ............... 128/272, 275, 276, 297, 128/760, 764, 766, 771; 73/729; 116/268, 270; 215/260, 261, 262

[56] References Cited

U.S. PATENT DOCUMENTS

| | | | |
|---|---|---|---|
| 2,957,609 | 10/1960 | Holmes | 128/272 UX |
| 3,874,367 | 4/1975 | Ayres | 128/766 |
| 3,939,835 | 2/1976 | Bridgman | 128/276 |
| 3,946,739 | 3/1976 | Berman et al. | 128/276 |

Primary Examiner—Robert W. Michell
Assistant Examiner—J. L. Kruter
Attorney, Agent, or Firm—Martin A. Farber

[57] ABSTRACT

The closure part is formed by a flat plug which is longitudinally displaceable within a nipple of the suction bottle, the flat plug being displaceable from its basic position on the outside of transverse openings of the nipple, past the transverse openings, into its closing position just in front of the inner end of the nipple, in which closing position it is located at a greater distance from the transverse openings than the length between an end edge and sealing place of a drainage-tube connecting plug serving as a ram for the flat plug.

11 Claims, 17 Drawing Figures

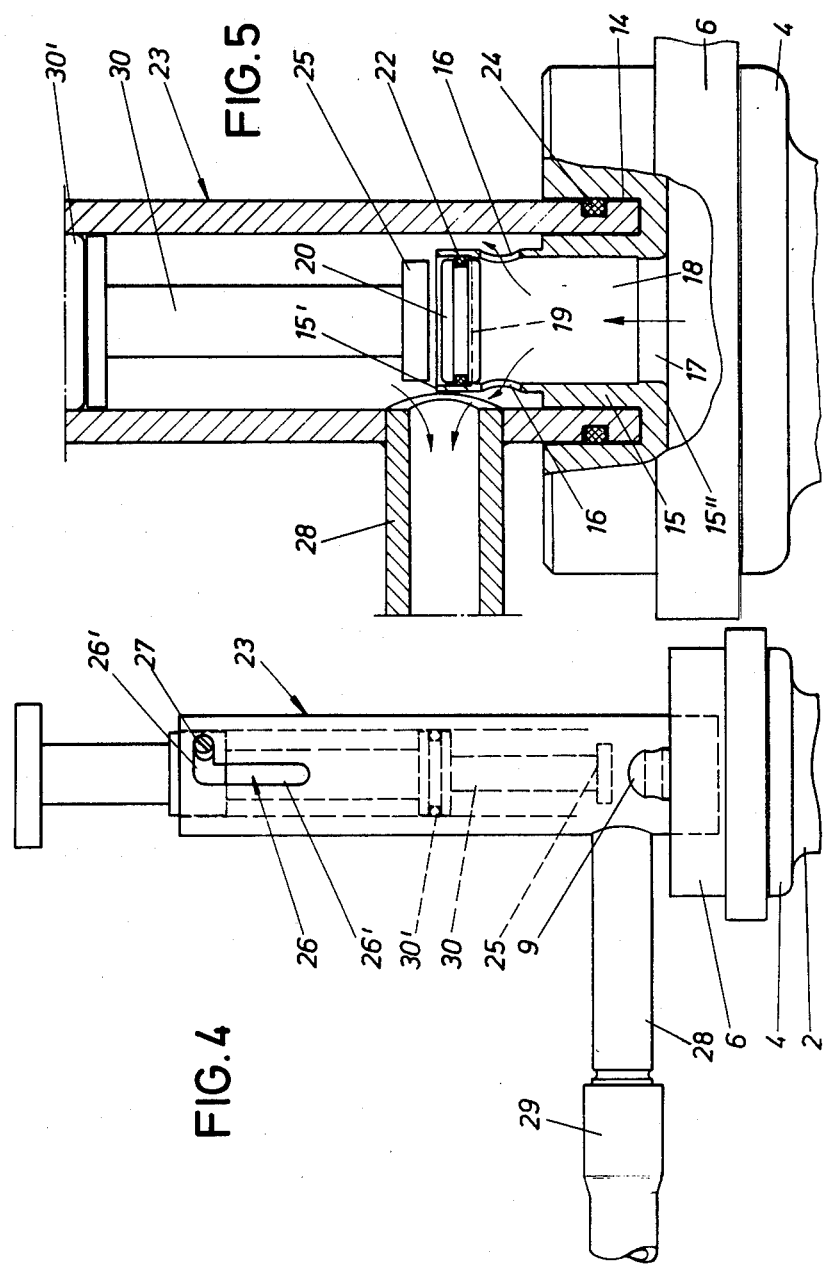

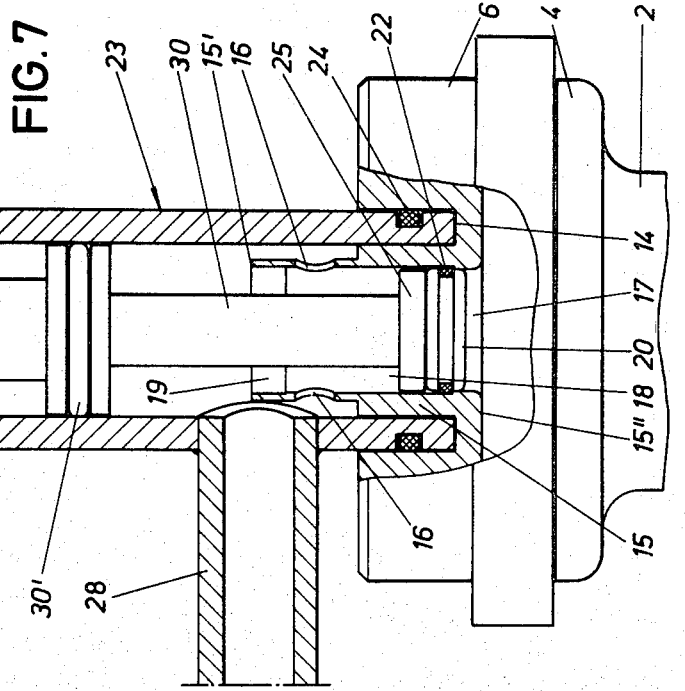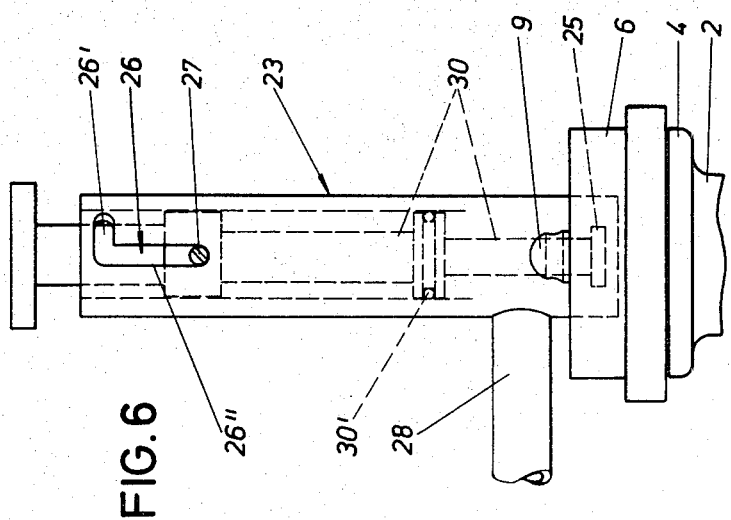

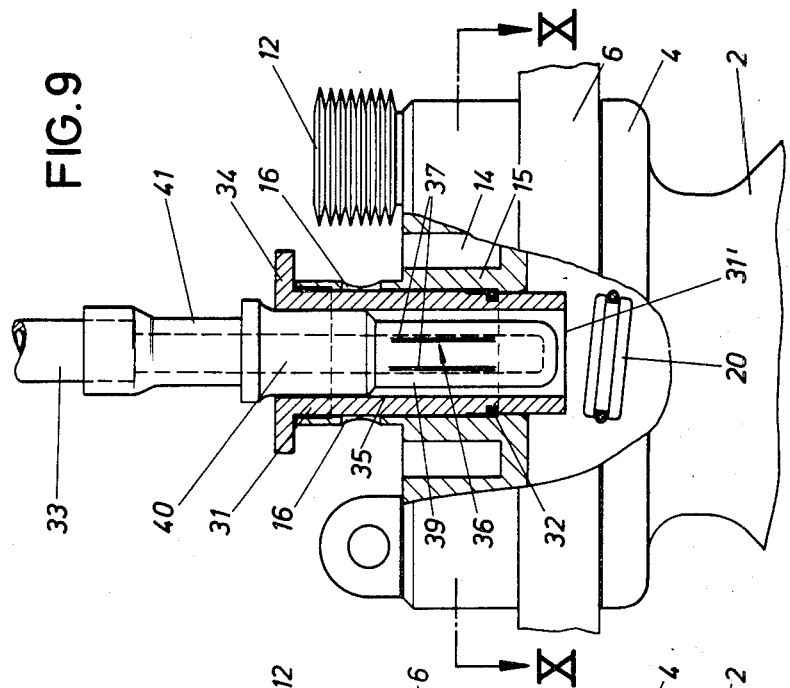
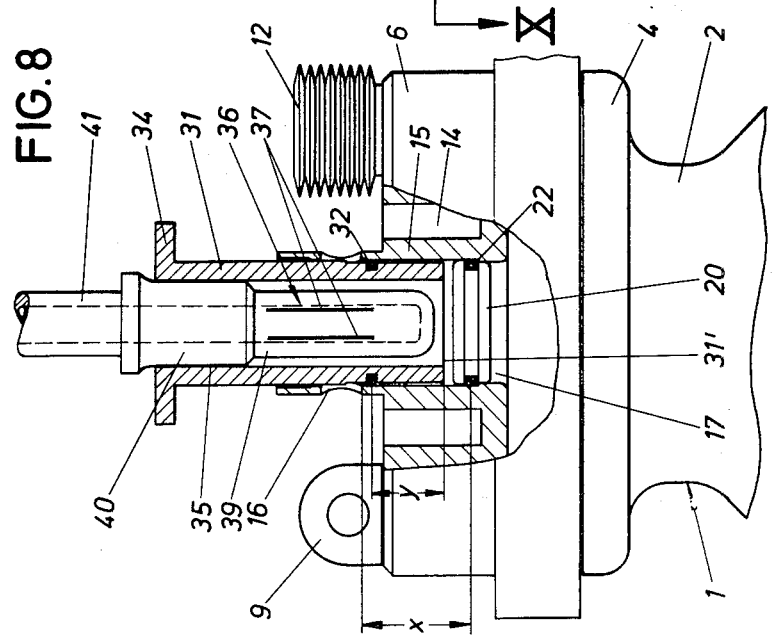

SUCTION BOTTLE FOR MEDICAL PURPOSES PARTICULARLY FOR THE CONNECTION OF DRAINAGE TUBES

The present invention relates to a suction bottle for medical purposes, and particularly for the connection of drainage tubes, it having a valve located in the drainage path, a shut-off part which can be brought into open position and a vacuum indicator.

Such suction bottles are known and are used in medicine for drawing secretions out of body cavities and as receiving vessels for blood donation. The bottles can be developed both as throwaway suction bottles and as resterilization suction bottles.

From German DE-OS No. 2 446 470 a resterilization suction bottle is known whose neck receives a sealable nipple in which there are contained two valves and a flow opening which is in communication with the drainage tube. During the pressure phase in the sterilizer, steam is introduced into the suction bottle through the one valve which is developed as an inlet valve, the steam being drawn off during the vacuum phase through the other valve which serves as an non-return valve. In the sterilization and vacuum phases the drainage tube is closed off by means of a tube clamp which crushes it. Such a suction bottle is difficult and therefore expensive to manufacture. Furthermore, it is always necessary to leave the drainage tube on the suction bottle during the sterilization. There is no assurance with it that the contents of the bottle cannot flow back through the drainage tube upon the occurrence of a lower pressure than that in the suction bottle.

The purpose of the invention is to provide a suction bottle of the type in question which is of economic construction and simple to manufacture in such a manner that while obtaining a simplified process of sterilization and evacuation, the structural parts are limited to a minimum.

This purpose is aided in its solution in the manner that the closure is formed by a flat plug (20, 21') which is longitudinally displaceable within a nipple (15, 55) of the suction bottle (1), the flat plug being displaceable from its base position on the outside of transverse openings (16, 16') of the nipple (15, 55) (FIGS. 2, 12, 16), past the transverse openings (16, 16'), into its closing position just in front of the inner end of the nipple (15, 55) (FIGS. 7, 14, 17), in which closing position it is located at a greater distance (x, x') from the transverse openings (16, 16') than the length (y, y') between end edge (31', 56') and the sealing place (32) of a drainage-tube connecting plug (31, 56), the latter serving as a ram for the flat plug (20, 21').

As a result of this formation there is established a suction bottle of the type in question which is characterized in particular by a simplified construction and by easier handling. The functions of the valve and of the shut-off parts are performed exclusively by the flat plug which is longitudinally displaceable in the nipple of the suction bottle. When the plug assumes its basic position, resterilization and evacuation of the suction bottle can be effected via the transverse openings in the plug. After the termination of this process the nipple can be displaced into its closing position. This means that the connection between the suction bottle and the transverse openings of the nipple is then interrupted. In this position the packing and transportation of the suction bottle is possible. The drainage-tube connecting plug can in this case possibly be inserted so far into the nipple that the end edge of the latter is located just in front of the flat plug. If connection is to be established between the drainage tube and the inside of the bottle, the drainage tube connecting plug need merely be pushed further inward, pushing the flat plug completely out of the nipple, the plug then falling into the inside of the bottle and not interfering there. The location of the flat plug in its closing position and the corresponding dimensioning of the connecting plug provide assurance that no outside air can flow into the inside of the bottle. Furthermore, the structural parts for the suction bottle are considerably reduced in number, which permits economical manufacture. Furthermore, the structural shape can be made very compact. The arrangement of the valve in the axial hollow in the connection plug also contributes to this. The flat plug, during its displacement, passes through three different zones of the nipple which are of different diameter. During evacuation or sterilization, the flat plug is located in the zone having the largest diameter. If it is then brought into the closing position, it travels through the central zone and comes right in front of the zone having the smallest diameter. This zone is so dimensioned that the vacuum is not capable of pulling the flat plug out of its position. This must be done intentionally, namely by the connecting plug. The evacuation of the suction bottle can be effected in simple manner by the suction head which can be placed on the nipple. A ram of this suction head makes it possible to push the flat plug through to such an extent after the evacuation of the bottle that it then assumes its closing position. The particular development of the valve connected to the drainage tube contributes to a further simplification of the overall construction of the suction bottle. The section of the tube which connects the drainage tube to the connecting plug as a result of its formation itself constitutes the coupling piece, which contributes towards reduction of the number of structural parts. The valve is made such that during the operation of the bottle, and even after the connecting plug has been removed from the suction bottle, secretions contained in the drainage tube cannot flow back. In order to couple the connecting plug with the tube section, the latter forms a plug-shaped intermediate section of widened cross section. If the drainage tube and connecting plug are removed from the suction bottle, the bottle can be sealed by means of a closure stopper. The latter is so developed that it closes not only the opening of the nipple but also the transverse openings thereof.

In a modified embodiment, the vacuum indicator, which is developed in the form of a bellows, is seated on the drainage-tube connecting plug. Accordingly, the closure cap need no longer itself directly bear the bellows. Accordingly, the passage channel in the closure cap is also done away with. The closure cap can be made of more compact shape, which also leads to a saving of material. During the sterilization and vacuum phases, the bellows is not located on the suction bottle so that there are also no disturbing projections on the suction bottle. The vacuum indicator becomes connected with the inside of the suction bottle only when the drainage-tube connecting plug is inserted into the nipple of the closure cap and in this connection pushes the flat plug into the inside of the suction bottle. By effecting this connection the atmospheric pressure pushes the bellows together and gives information concerning the vacuum in the suction bottle.

One advantageous structural shape consists in having the bellows seated on the drainage-tube connecting plug in a transverse position. A transverse bore need merely be provided on the drainage-tube connecting plug for the bellows. Nevertheless, the bellows does not protrude beyond the outer dimension of the suction bottle so that the bellows is substantially protected from impacts.

In addition to this, it is advantageous for an additional bellows to be seated on the flat plug. This has the advantage that even at the time of the delivery of the suction bottle and before it is placed in use, the user can note whether the vacuum is present. If the drainage-tube connecting plug is seated in the closure cap, the flat plug with its bellows falls into the inside of the bottle.

Finally, it is also advantageous for the bellows to have a connection insertion collar. The edge of this insertion collar goes into operation when the bellows is inserted into the transverse bore of the drainage-tube connecting plug. The edge limits the insertion path and holds the bellows in a proper operation position.

With the above and other objects and advantages in view, the present invention will become more clearly understood in connection with the detailed description of preferred embodiments when considered with the accompanying drawings, of which:

FIG. 4 is a view of the upper region of the suction bottle with suction head attached, corresponding to the evacuation position of the head.

FIG. 5 shows, on a larger scale, a longitudinal section through the nipple and suction head during the evacuation.

FIG. 6 is a showing which corresponds to FIG. 4 but in which the ram of the suction head has been brought into a different end position in order to displace the flat plug.

FIG. 7 is a showing which corresponds to FIG. 5 and shows the position of the flat plug displaced by the ram of the suction head.

FIG. 8 shows, on a larger scale, the upper region of the suction bottle with the flat plug in closing position and the drainage-tube connecting plug partially introduced, its sealing point being located below the transverse opening of the nipple.

FIG. 9 is a showing corresponding to FIG. 8 with the drainage-tube connecting plug fully inserted.

Figure 1:
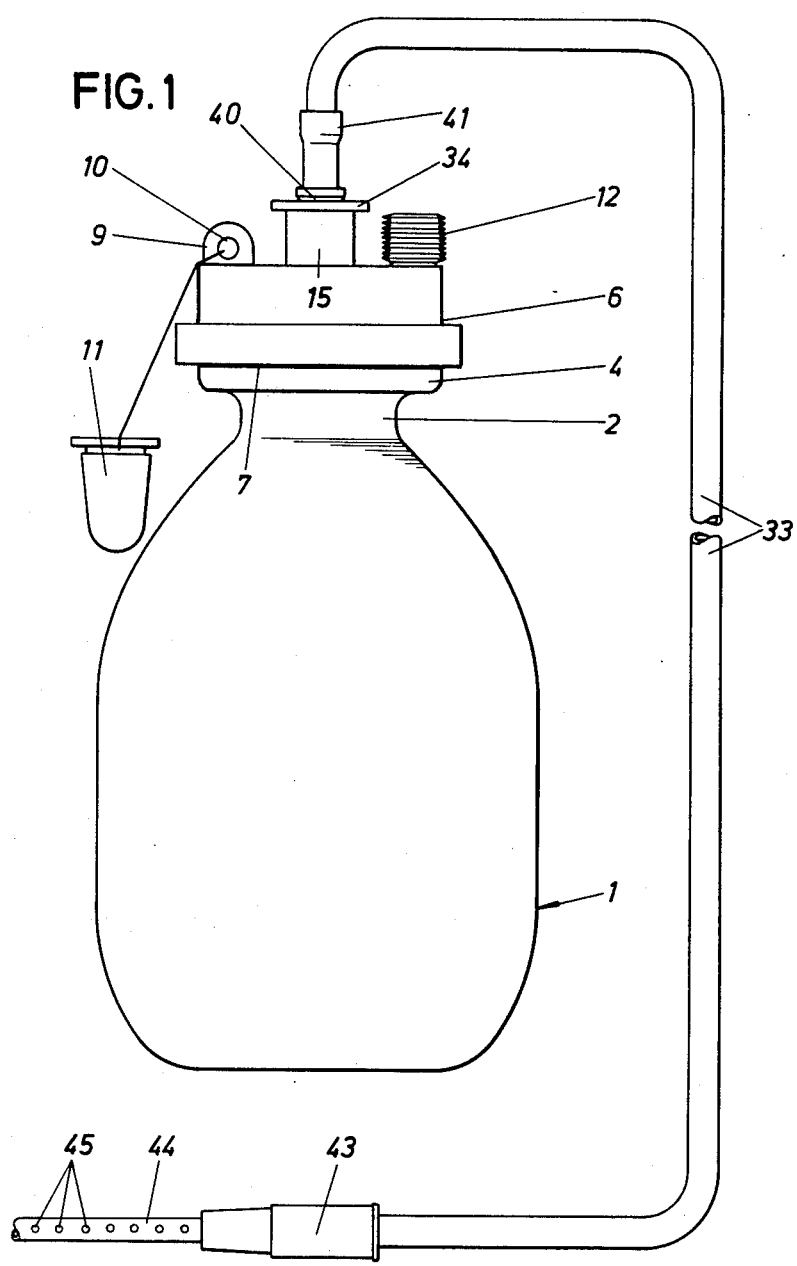
FIG. 1 is a view of a suction bottle with connected drainage tube, in accordance with the first embodiment.

The suction bottle which is shown in its entirety in FIG. 1 has a bottle body which continues into a bottle neck 2. The latter extends and widens to form a flange 4 which receives a sealing 3 and an externally threaded section 5 which is adjacent the flange. Over the threaded section 5 there is a closure cap 6 which can be screwed on and has a manipulating ring, the end edge 7 of the closure cap 6 coming against the sealing ring 3.

The closure cap 6 is provided with an attachment body 9. A borehole 10 therein makes it possible, for instance, to hang the suction bottle from a supporting arm or to pass a suspension cord through it. At this place also the closure plug 11, described further below can be detachably fastened as indicated in FIG. 1.

Diametrically opposite the attachment member 9 there is a known vacuum indicator 12 which is in communication with the inside of the bottle via a passage channel 13.

Figure 2:
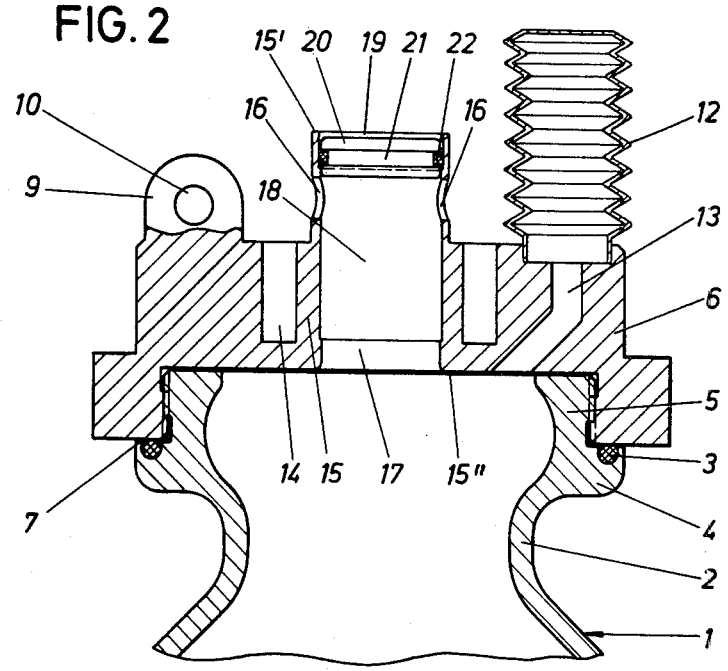
FIG. 2 shows, on a larger scale, a longitudinal section through the upper region of the suction bottle with a plug in its basic position before the evacuation of the suction bottle.
Figure 3:
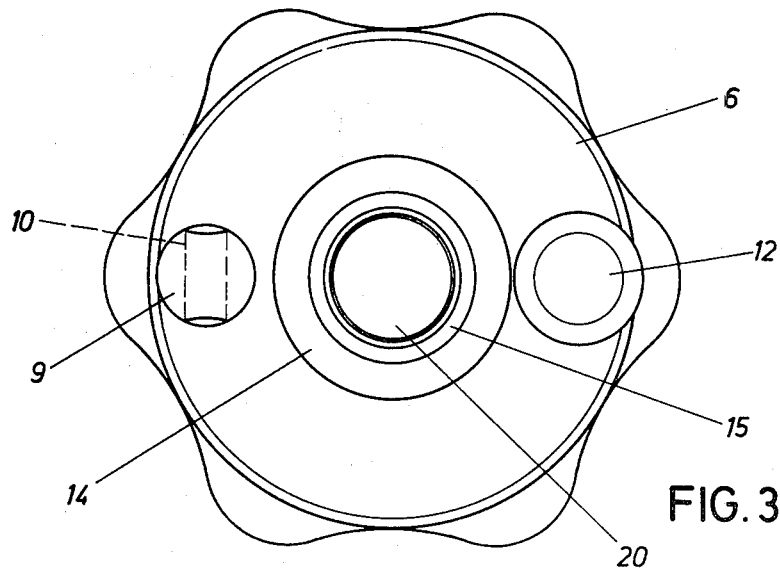
FIG. 3 is a top view of FIG. 2.
Figure 10:
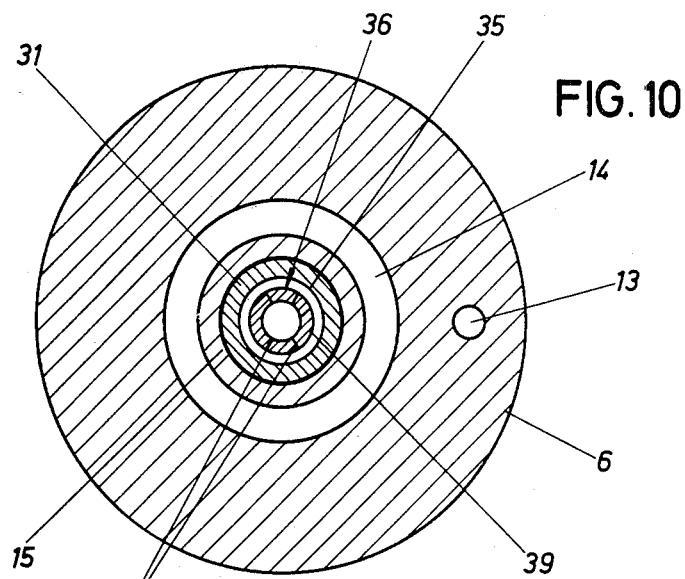
FIG. 10 is a section along the line X—X of FIG. 9.

From the top of the closure cap 6 there extends an annular groove 14 which surrounds a central nipple 15. The nipple 15 protrudes beyond the top of the closure cap 6 and is provided there with two diametrically opposite transverse openings 16. As shown in particular in FIG. 2, the inner wall of the nipple 15 has three zones 17, 18 and 19 which are stepped down with respect to each other in such a manner that the outer zone 19 of the nipple has the largest diameter. Before the evacuation of the suction bottle 1, a flat plug 20 is present in the zone 19, the plug carrying, in a central groove 21, a sealing ring 22 which bears against the inner wall of the zone 19.

For the evacuation of the suction bottle 1, the suction head 23 is placed on the nipple 15 (FIGS. 4, 5), the lower end (provided with a sealing ring 24) of the suction head 23 extending into the annular groove 14. In this position the plate 25 of the ram 30 which is displaceably guided in the suction head terminates just in front of the upper end edge 15' of the nipple 15 or just in front of the flat plug 20. A grub screw pin 27 which extends from the ram 30 and passes through an angular slot 26 in the suction head 23 secures the ram 30 in its position. In the region between the grub screw pin 27 and the plate 25 the ram 30 carries a sealing ring 30'. During the evacuation therefore air can be drawn out only from the suction bottle. In the vicinity of the lower end of the suction head 23 there extends in transverse direction from same an exhaust nipple 28 which is connected via a hose or flexible tube 29 with a vacuum generator, not shown. During the evacuation, the grub screw pin 27 of the ram 30 is in the horizontally directed section 26' of the slot so that no undesired displacement of the ram 30 takes place.

After evacuation of the suction bottle, the ram 30 is turned to such an extent that its grub screw pin 27 comes against the other wall of the horizontally extending section 26' of the slot and permits downward displacement of the ram 30 into the position shown in FIG. 6. The downward displacement of the ram is limited by the length of the vertically arranged section 26" of the slot. The ram 30 has then however, via its plate 25, moved the flat plug 20 into the closing position, as shown in FIGS. 7 and 8, in which the sealing ring 22 of the flat plug 20 still lies within the zone 18 but close to the point of transition to the zone 17 of smaller cross section. As a result of suitable dimensioning of the zone 17, the flat plug 20 can be located a short distance in front of the inner end 15" of the nipple 15. The suction head 23 can then be taken off.

The drainage-tube connecting plug 31 can now be inserted into the inside of the nipple 15 in such a manner that its end edge 31' terminates just in front of the flat plug 20; see FIG. 8. In this position, the sealing place 32 of the drainage-tube connection plug 31, which sealing place is formed by a sealing ring, also lies below the transverse openings 16 of the nipple. However, there is no connection between the drainage tube 33 extending from the connection plug 31 and the suction bottle.

From FIG. 8 it can furthermore be noted that the distance x of the flat plug 20 from the transverse openings 16 is greater than the length y between the end edge 31' of the connecting plug 31 and the sealing place 32. If the drainage tube 33 is now to be connected with the inside of the suction bottle, the connection plug 31 must be pushed in completely. Its end flange 34 strikes against the outer end edge 15' of the nipple 15 and limits the displacement movement. Upon this operation the flat plug 20, acted on by the end edge 31', passes through the zone 17 of smallest cross section of the inner wall of the nipple 15 and drops into the inside of the bottle.

The valve 36 which leads to the drainage tube 33 is arranged in the axial cavity 35 of the connecting plug 31. This valve is formed by a tube section 39 closed at its end and provided with longitudinal slots 37. The tube section 39 which passes into an intermediate section 40 which is widened in cross section in plug shape consists of flexible material so that no additional structural parts are required for this valve.

Adjoining the intermediate section 40 there is also a connecting section 41 into which the end of the drainage tube 33 is inserted. This end of the drainage tube 33 can also be inserted directly (without connection section 41) into the intermediate section 40. An end connection piece 43 thereof can be connected with the drainage-tube section 44 located in the body cavity, this section having the transversely directed suction holes 45. Due to this connecting piece 43 and the connection section 41 the tube section lying between these parts represents a separate drainage-tube connection section.

Figure 11:
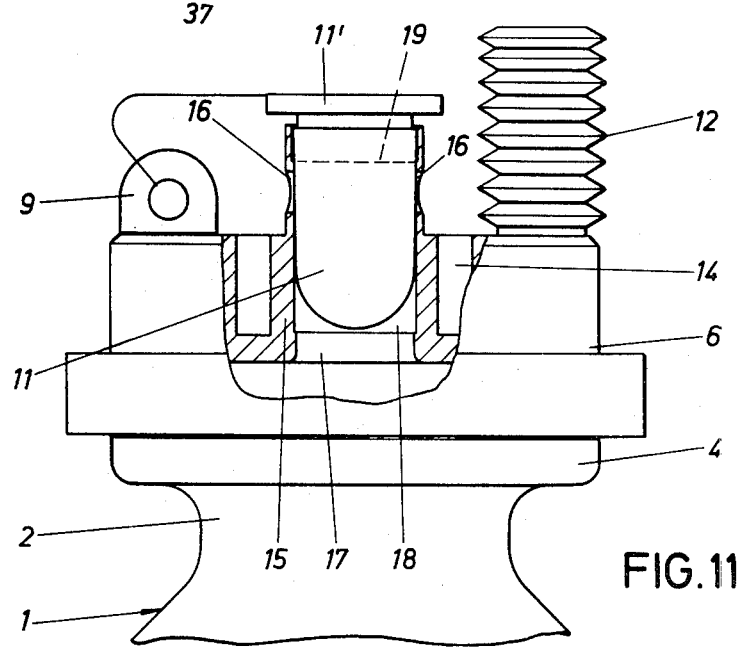
FIG. 11 shows the upper region of the suction bottle on a larger scale with the drainage-tube connection plug removed and the closure plug inserted into the nipple.

When the suction bottle is evacuated, the vacuum indicator 12 assumes the position shown in FIGS. 1, 8 and 9. If the vacuum upon use becomes too low, this is made evident by the vacuum indicator which is then in the position shown in FIG. 11. The connecting plug 31 can now be pulled out of the nipple 15. The valve 36 prevents any wound secretions present in the drainage tube 33 from then flowing back.

The suction bottle can be closed by the closure plug 11. The latter is so developed that it seals not only the opening of the nipple 15 but also the transverse openings 16 thereof. An end flange 11' facilitates the handling of the closure plug 11. After resterilization of the suction bottle 1 and application of the flat plug 20, the previously described process can be carried out again.

In the case of a throw-away suction bottle, the closure cap 6 is cemented hermetically onto the flange 4 without the use of a sealing ring 3.

Figure 12:
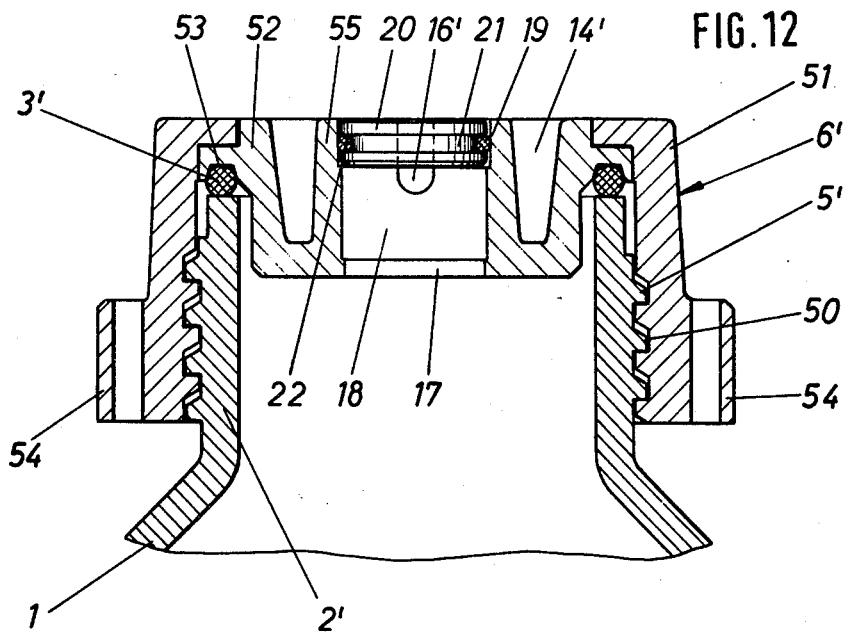
FIG. 12 shows on an enlarged scale a longitudinal section through the upper region of a suction bottle in accordance with the second embodiment with a flat plug in its basic position prior to the evacuation of the suction bottle.
Figure 13:
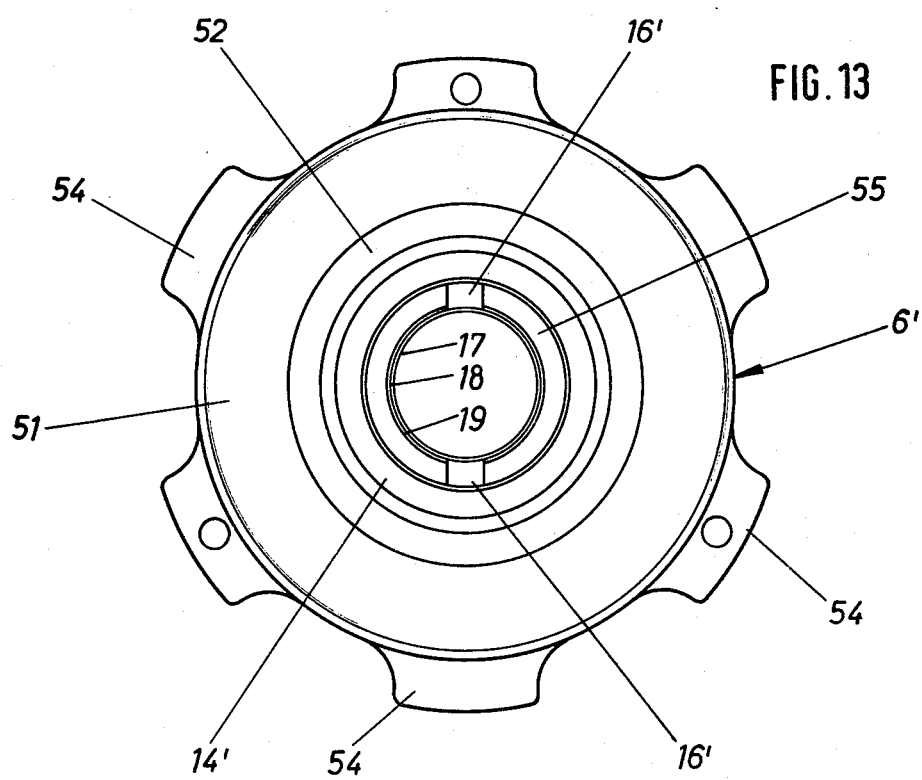
FIG. 13 is a top view of FIG. 12.

The suction bottle shown in part in FIG. 12 has a bottle body 1 which is continued by the bottle neck 2'. The latter forms an outer thread 5' which is connected with the inner thread 50 of a two piece closure cap 6'. The latter comprises a collar-like ring 51 and an insert piece 52 which lies therein. The ring 51 extends over the edge region of the insert member 52, a sealing ring 3' being present in the annular groove 53 of the insert member. When the closure cap 6' is screwed-on, the sealing ring 3' is pressed against the end edge of the bottle neck 2'. Grip projections 54 which are arranged spaced at uniform angles apart and extend from the lower edge of the ring 51 serve to assist in the screwing-on.

From the top of the closure cap 6' there extends an annular groove 14' which surrounds a central nipple 55. Within the nipple 55, which terminates flush with the end surface of the closure cap, there are two diametrically opposite transverse openings 16'.

From FIG. 12 it can be seen that the inner wall of the nipple 55 has zones 17, 18 and 19 which are reduced stepwise, the upper zone 19 having the largest diameter. Before the evacuation of the suction bottle 1, the flat plug 20 is in the zone 19, the plug holding in a central groove 21, a sealing ring 22 which bears against the inner wall of the zone 19.

Figure 14:
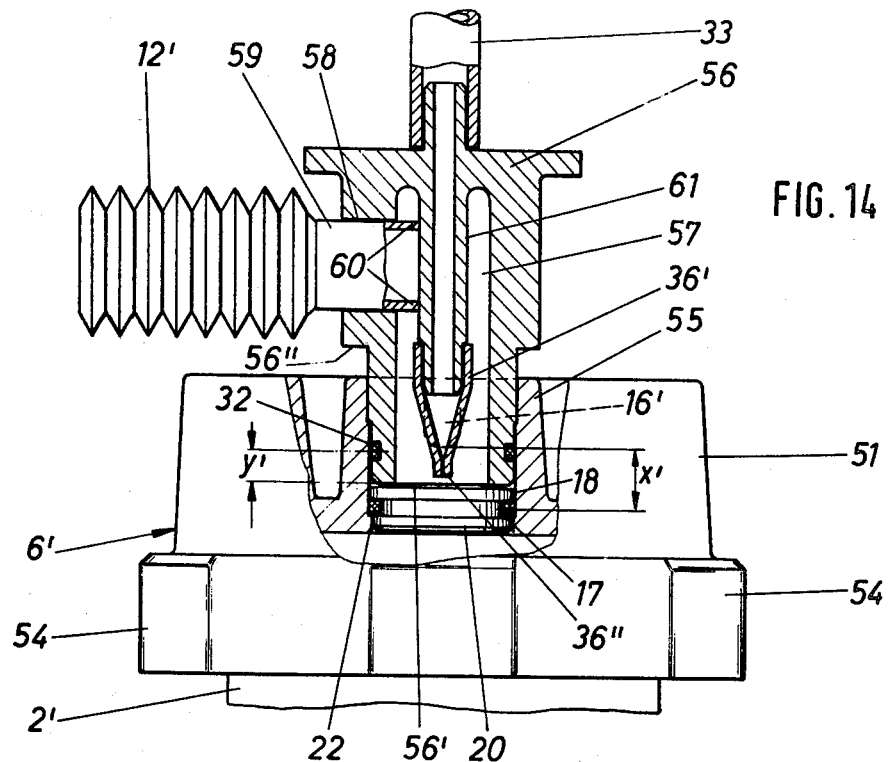
FIG. 14 shows on a larger scale the upper region of the suction bottle with the flat plug in closing position and the drainage-tube connecting plug partially introduced, its point of sealing lying below the transverse opening of the nipple.

After the evacuation of the suction bottle, which is effected through the transverse openings 16', the flat plug 20 is moved by a suction head similar to suction head 23 of the previous embodiment, here not shown in detail, into the closing or sealing position shown in FIG. 14, in which position the sealing ring 22 of the flat plug 20 still lies within the zone 18 but now close to the place of transition to the zone 17 of smaller cross section.

The drainage-tube connecting plug 56 can now be inserted into the inside of the nipple 55 in such a manner that the end edge 56' of the plug terminates just above the flat plug 20; see FIG. 14. In this position, the sealing place 32 of the drainage-tube connecting plug 56, which sealing place is formed by a sealing ring, is also located below the transverse openings 16' of the nipple 55. However, there is still no communication between the suction bottle 1 and the drainage tube 33 which extends from the connecting plug 56.

From FIG. 14 it can be noted that the distance x' of the flat plug 20 from the transverse opening 16' is greater than the length y' between the end edge 56' and the sealing place 32.

The drainage-tube connecting plug 56 is provided with a cavity 57 which extends from its end edge 56'. Into this cavity there communicates a transverse borehole 58, into which the vacuum indicator 12', developed in the form of a bellows, is inserted by means of an insertion collar 59. The front edge 60 of the collar comes against and is stopped by a central pipe 61 of the drainage-tube connecting plug 56, which pipe extends into the cavity 57.

The valve 36' which leads to the drainage tube 33 is arranged in the cavity 57. This valve is placed onto the end of the pipe 61 and is provided at its end with the sealing lips 36" which come against each other.

Figure 15:
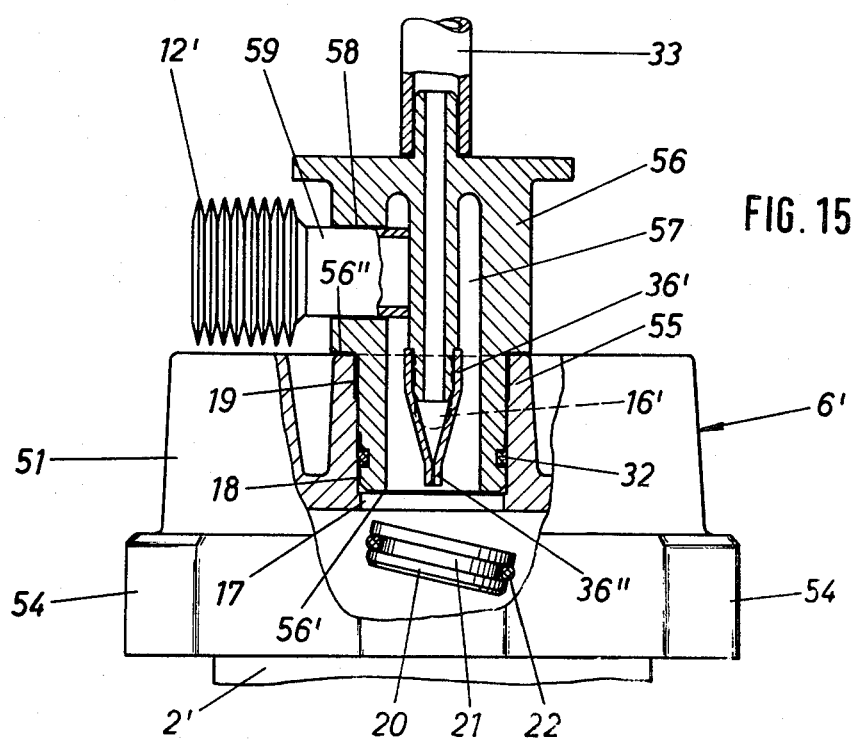
FIG. 15 is a showing corresponding to FIG. 14 but with the drainage-tube connecting plug fully inserted, pressing the flat plug into the inside of the bottle.

If communication is now to be established between the drainage tube 33 and the inside of the suction bottle, the connecting plug 56 is pushed in completely. Its step 56" strikes against the outer end edge of the nipple 55 and limits the displacement movement. In this operation the flat plug 20 which is engaged by the end edge 56' passes through the zone 17 of smallest cross section of the inner wall of the nipple 55 and drops into the inside of the bottle; see FIG. 15. In this way the bellows 12' is also in communication with the inside of the bottle and is compressed as a result of the atmospheric pressure. As the vacuum becomes weaker, the bellows 12' or vacuum indicator expands. Replacement of the suction bottle is then necessary. After the drainage-tube connecting plug 56 has been pulled out, the valve 36' prevents the wound secretion present in the drainage tube 33 from flowing backward.

Figure 16:
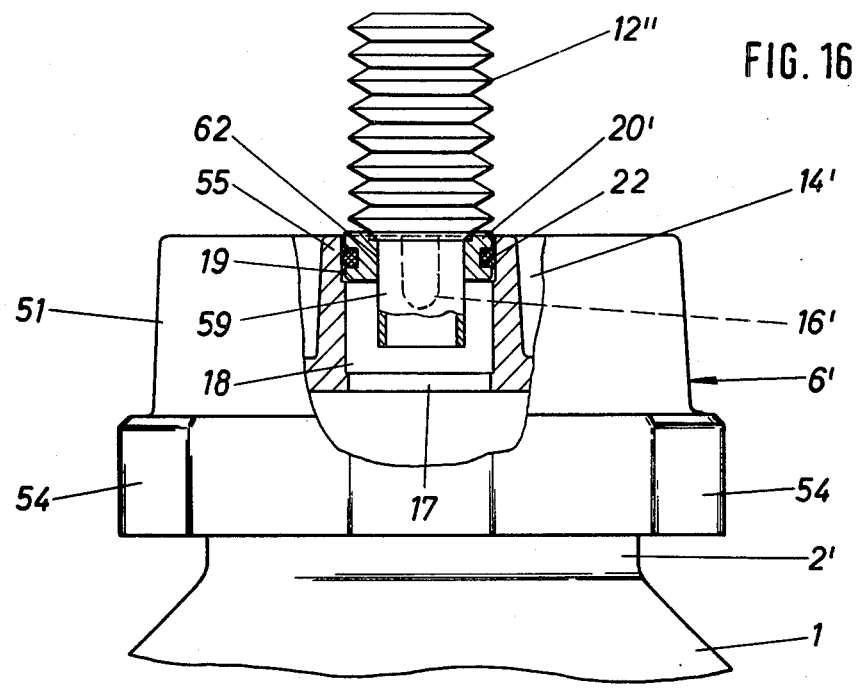
FIG. 16 is a partial section through the upper region of the suction bottle with a flat plug in the basic position, it bearing a bellows.
Figure 17:
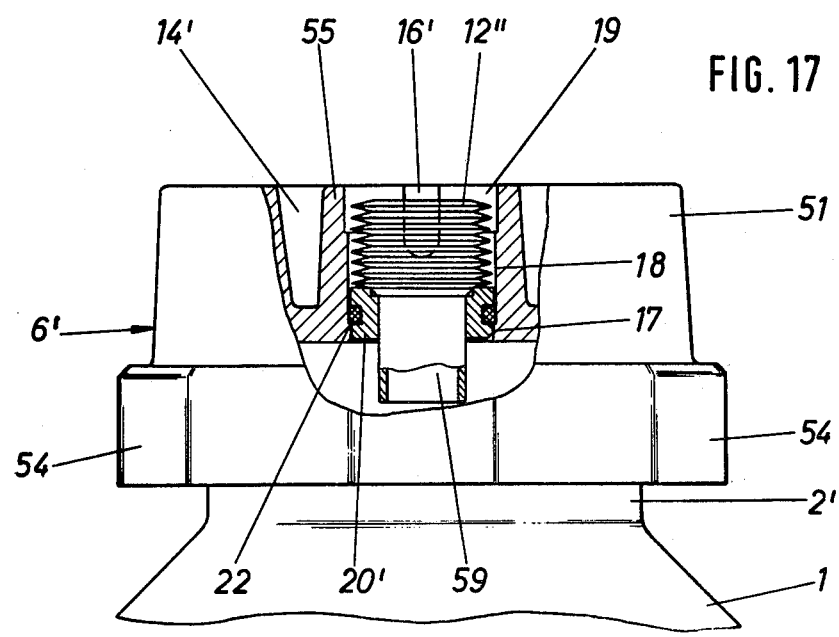
FIG. 17 is a showing corresponding to FIG. 16 but with the flat plug in closing position.

The construction of the suction bottle described in FIGS. 16 and 17 corresponds to that of the preceding embodiments and the same numerals are used for corresponding parts which are not here again described. The flat plug 20' is merely shaped differently. It has a central borehole 62 into which the insertion collar 59 of a vacuum indicator 12" is inserted. Before the evacuation, the flat plug 20' assumes the position shown in FIG. 16. The suction bottle can now be evacuated through the transverse openings 16'. After the evacuation has been completed the flat plug 20' is moved into the closing position shown in FIG. 17. The bellows 12" thus contract. The bellows is then arranged completely within the nipple 55 and does not extend beyond the end surface of the closure cap 6'.

If the suction bottle is to be inserted, then the flat plug 20' together with bellows 12" is pushed into the inside of the bottle by means of the drainage-tube connection nipple 56.

The bellows 12" gives information as to the vacuum in the suction bottle when the flat plug 20' is in the closing position.

I claim:

1. In a suction bottle for medical purposes, and particularly for the connection of drainage tubes, having a valve located in the drainage path, a closure part which can be brought into an open position and a vacuum indicator, the improvement comprising
   a flat plug constituting the closure part,
   a nipple communicating with an interior of the suction bottle, said nipple being formed with transverse openings and having an inner end,
   said flat plug being disposed longitudinally displaceable within said nipple of the suction bottle, said flat plug being displaceable in said nipple, from a basic position thereof on the outside of said transverse openings of the nipple whereby the transverse openings communicate via said nipple with the interior of the suction bottle, inwardly past said transverse openings into a closing position just in front of the inner end of said nipple,
   a drainage-tube connecting plug removeably positioned in said nipple and having a sealing place sealingly engaging said nipple and an end edge constituting a ram for pushing said flat plug inwardly into said interior of the suction bottle,
   said flat plug in said closing position being located at a greater distance from said transverse openings than the distance between said end edge and said sealing place of said drainage-tube connecting plug.

2. The suction bottle according to claim 1, wherein said connecting plug defines an axial hollow,
   the valve in the drainage path for a drainage tube is disposed in said axial hollow.

3. The suction bottle according to claim 2, wherein the valve is formed of a tube section closed at an end thereof and formed with longitudinal slots, said tube section constitutes a coupling piece between said connecting plug and the drainage tube.

4. The suction bottle according to claim 3, wherein said tube section has an intermediate section of a cross-section widened in the form of a plug.

5. The suction bottle according to claim 1, wherein said nipple has an inner wall,
   said inner wall is stepped down in different diameters, becoming smaller in the inwardly direction towards said inner end of said nipple.

6. The suction bottle according to claim 1, further comprising
   a closure cap of the suction bottle,
   said nipple projects at a top of said closure cap of the suction bottle and defines therearound with said closure cap an annular groove,
   a suction head means releaseably sealingly disposed in said annular groove and for suction evacuation communication with said transverse openings and via thereby with the interior of the suction bottle, said suction head means includes a ram means for pushing said flat plug inwardly into said nipple into said closing position after the evacuation communication.

7. The suction bottle according to claim 1, further comprising
   a closure plug means for being removeably sealingly disposed in said nipple and extending therein to above said transverse openings and coordinated with an outside end of said nipple.

8. The suction bottle according to claim 1, further comprising
   a vacuum indicator constituting a bellows is mounted on said drainage-tube connecting plug.

9. The suction bottle according to claim 8, wherein said bellows is mounted in a transverse position on said drainage-tube connecting plug.

10. The suction bottle according to claim 8, further comprising
    an additional bellows is mounted on said flat plug.

11. The suction bottle according to claim 8, wherein said bellows has a connecting insertion collar communicating therewith and extending through said flat plug communicating with the interior of the suction bottle.

* * * * *